United States Patent
Li

(10) Patent No.: US 10,300,474 B2
(45) Date of Patent: May 28, 2019

(54) CATALYSTS FOR CONVERSION OF 2,3-BUTANEDIOL-CONTAINING FERMENTATION MIXTURE TO HYDROCARBONS

(71) Applicant: UT-Battelle, LLC, Oak Ridge, TN (US)

(72) Inventor: Zhenglong Li, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 16/059,512

(22) Filed: Aug. 9, 2018

(65) Prior Publication Data

US 2019/0046967 A1    Feb. 14, 2019

Related U.S. Application Data

(60) Provisional application No. 62/545,070, filed on Aug. 14, 2017.

(51) Int. Cl.
   *C07C 1/20*        (2006.01)
   *C07C 1/24*        (2006.01)
   (Continued)

(52) U.S. Cl.
   CPC ........... *B01J 35/0006* (2013.01); *B01J 21/04* (2013.01); *B01J 21/063* (2013.01); *B01J 21/066* (2013.01);
   (Continued)

(58) Field of Classification Search
None
See application file for complete search history.

(56) References Cited

U.S. PATENT DOCUMENTS

| | | | |
|---|---|---|---|
| 2006/0057058 A1* | 3/2006 | Dahl | C01B 3/382 423/648.1 |
| 2015/0218062 A1* | 8/2015 | Lilga | C07C 29/60 568/903 |

(Continued)

OTHER PUBLICATIONS

Roth W.J. et al., "Two-Dimensional Zeolites: Current Status and Perspectives", Chemical Reviews, (2014), vol. 114, pp. 4807-4837 dx.doi.org/10.1021/cr400600f.

(Continued)

*Primary Examiner* — Philip Y Louie
(74) *Attorney, Agent, or Firm* — Scully Scott Murphy & Presser

(57) ABSTRACT

A method for producing one or more hydrocarbon compounds from at least one of 2,3-butanediol, acetoin, and ethanol, the method comprising contacting said at least one of 2,3-butanediol, acetoin, and ethanol with a catalyst at a temperature of at least 100° C. and up to 500° C. to result in said 2,3-butanediol, acetoin, and/or ethanol being converted to said one or more hydrocarbon compounds, wherein said catalyst is either: (i) a catalyst comprising nanoparticles composed of (a) a first metal oxide selected from the group consisting of zirconium oxide, cerium oxide, titanium oxide, and lanthanum oxide, and (b) a main group metal oxide; or (ii) a catalyst comprising a zeolite loaded with at least one metal selected from the group consisting of copper, silver, nickel, palladium, platinum, rhodium, and ruthenium in an amount of 1-30 wt % by weight of the zeolite.

21 Claims, 7 Drawing Sheets

(51) Int. Cl.
| | |
|---|---|
| *B01J 35/00* | (2006.01) |
| *B01J 21/04* | (2006.01) |
| *B01J 21/06* | (2006.01) |
| *B01J 21/08* | (2006.01) |
| *B01J 23/10* | (2006.01) |
| *C07C 31/10* | (2006.01) |
| *B01J 29/46* | (2006.01) |
| *B01J 29/70* | (2006.01) |
| *C07C 15/46* | (2006.01) |
| *C07C 49/10* | (2006.01) |
| *C07C 11/167* | (2006.01) |
| *C07C 11/08* | (2006.01) |
| *B01J 29/44* | (2006.01) |

(52) U.S. Cl.
CPC ............. *B01J 21/08* (2013.01); *B01J 23/10* (2013.01); *B01J 29/44* (2013.01); *B01J 29/46* (2013.01); *B01J 29/7038* (2013.01); *C07C 11/08* (2013.01); *C07C 11/167* (2013.01); *C07C 15/46* (2013.01); *C07C 31/10* (2013.01); *C07C 49/10* (2013.01)

(56) References Cited

U.S. PATENT DOCUMENTS

2015/0284307 A1* 10/2015 Lilga .................. C07C 45/52
568/881
2017/0342009 A1* 11/2017 Song .................. C07C 1/24

OTHER PUBLICATIONS

Srdic V.V. et al., "Recent progress on synthesis of ceramics core/shell nanostructures", Processing and Application of Ceramics, (2013), vol. 7, pp. 45-62.

Cho S. et al., "Enhanced 2,3-Butanediol Production by Optimizing Fermentation Conditions and Engineering Klebsiella oxytoca M1 through Overexpression of Acetoin Reductase", PLoS ONE, (2015), 10(9), e0138109, 16 pages DOI:10.1371/journal.pone.0138109.

Diaz U. "Layered Materials with Catalytic Applications: Pillared and Delaminated Zeolites from MWW Precursors" ISRN Chemical Engineering, (2012), vol. 2012, Article ID 537164, 35 pages doi:10.5402/2012/537164.

Garg S.K. et al., "Fermentative Production of 2,3-Butanediol: A Review", Bioresource Technology, (1995), 51, pp. 103-109.

Ji X. et al., "Microbial 2,3-butanediol production: A state-of-the-art review", Biotechnology Advances, (2011), 29, pp. 351-364 doi:10.1016/j.biotechadv.2011.01.007.

Sagadevan S. et al., "Hydrothermal synthesis of zirconium oxide nanoparticles and its characterization", Journal of Materials Science: Materials in Electronics, (2016), 27, pp. 5622-5627 DOI 10.1007/s10854-016-4469-6.

Selvi N. et al., "Synthesis, structural and optical characterization of ZrO2 core—ZnO@SiO2 shell nanoparticles prepared using co-precipitation method for opto-electronic applications", Journal of Materials Science: Materials in Electronics, (2014), 25, pp. 5078-5083 DOI 10.1007/s10854-014-2274-7.

* cited by examiner

CATALYSTS FOR CONVERSION OF 2,3-BUTANEDIOL-CONTAINING FERMENTATION MIXTURE TO HYDROCARBONS

CROSS REFERENCE TO RELATED APPLICATION

The present application claims the benefit of U.S. Provisional Application No. 62/545,070, filed on Aug. 14, 2017, all of the contents of which are incorporated herein by reference.

GOVERNMENT SUPPORT

This invention was made with government support under Prime Contract No. DE-AC05-00OR22725 awarded by the U.S. Department of Energy. The government has certain rights in the invention.

FIELD OF THE INVENTION

The present invention relates, generally, to the catalytic conversion of butanediols to hydrocarbons, and more particularly, to such catalytic conversion effected by core-shell nanoparticle catalysts and zeolite-based catalysts.

BACKGROUND OF THE INVENTION

Biomass fermentation to butanediols (particularly 2,3-butanediol) is an important biological conversion pathway since butanediols are highly useful chemical building blocks for the production of a range of chemicals, including methyl ethyl ketone (MEK), 1,3-butadiene, and gamma-butyrolactone. Biomass fermentation to butanediols is generally accompanied by the co-production of acetoin and ethanol in water. Water content can be up to 90% in a typical butanediol fermentation mixture.

Methods currently exist for converting butanediols to hydrocarbon fuels by the action of specialized catalysts. However, the conventional catalysts used for conversion of butanediols to hydrocarbon fuel are significantly hindered by the presence of the many co-products aside from butanediols (e.g., acetoin and ethanol) in butanediol fermentation mixtures. Thus, many efforts have been made to separate the butanediols from the other co-products. However, due to the high boiling points of butanediols and acetoin, separation of butanediols from other co-products is very challenging and costly. Thus, there would be a significant benefit in a process that could directly convert the mixture of products found in a typical butanediol fermentation mixture to liquid hydrocarbon fuels, which would eliminate the need to first separate the butanediols from the other co-products. Moreover, in such a process the resulting hydrocarbon fuels can be readily separated from the aqueous solution in which the reactant molecules reside.

SUMMARY OF THE INVENTION

The invention is directed to methods for catalytically converting at least one of 2,3-butanediol (2,3-BDO), acetoin, and ethanol to one or more hydrocarbon compounds, such as methyl ethyl ketone, alkenes containing 2-8 carbon atoms, 1,3-butadiene, and 2-methylpropanal. Although the catalysts described herein can accomplish the conversion of 2,3-butanediol, acetoin, or ethanol in their pure states, either in the presence or absence of water, it is significant for purposes of the present invention that the catalysts described herein can effectively convert a mixture of these compounds, as found in a butanediol fermentation mixture, to one or more hydrocarbons. Thus, in contrast to the conventional process, the catalysts described herein can advantageously accomplish such conversion without separation of butanediols from other co-products normally found in a butanediol fermentation mixture.

In a first embodiment, the catalyst contains nanoparticles composed of (a) a first metal oxide selected from the group consisting of zirconium oxide, cerium oxide, titanium oxide, and lanthanum oxide, and (b) a main group metal oxide. In a second embodiment, the catalyst contains a zeolite loaded with at least one metal selected from the group consisting of copper, silver, nickel, palladium, platinum, rhodium, and ruthenium in an amount of 1-30 wt % by weight of the zeolite. In the process, at least one of 2,3-butanediol, acetoin, and ethanol is contacted with either of the above two catalysts at a temperature of at least 100° C. and up to 500° C. to result in the 2,3-butanediol, acetoin, and/or ethanol being converted to one or more hydrocarbon compounds. In some embodiments, the conversion process is conducted on a butanediol fermentation mixture, which contains at least 2,3-butanediol, acetoin, and ethanol.

In particular embodiments, the catalyst is composed of nanoparticles having a core-shell $SiO_2@ZrO_2$ (i.e., a $SiO_2$ core and $ZrO_2$ shell) for conversion of a 2,3-BDO fermentation mixture to hydrocarbons (fuel intermediate), solvents, or other chemicals. This type of catalyst has a very good hydrothermal stability and can tolerate water at high temperatures, e.g., up to 700° C. This catalyst is able to convert a mixture of 2,3-BDO, acetoin and ethanol (or 2,3-BDO and acetoin) to $C_2$-$C_4$ mixed olefins (dominated by butenes), 2-methyl propanal, acetone, methyl ethyl ketone, 1,3-butadiene, styrene, and xylenes. Both acetone and methyl ethyl ketone (MEK) are commercially important solvents, while styrene & xylenes are important chemicals for polymer applications, and 1,3-butadiene is an important industrial chemical for the production of synthetic rubber. The direct conversion of butanediol fermentation mixtures using this catalyst without product separation from water provides a cost-effective approach for the hydrocarbon conversion of butanediol fermentation mixtures. This catalyst is also able to convert both acetoin and ethanol, besides 2,3-BDO, which greatly increases the carbon recovery into the final products. The $C_2$-$C_4$ mixed olefins can be further oligomerized via acid catalysts and then hydrogenated to jet fuels. 2-Methyl propanal (a fuel additive) can also be converted to jet fuel via condensation and hydrodeoxygenation. When copper is included on the core-shell materials, the yield of butenes can be greatly improved and jet fuel production will increase. The amount of jet fuel production, solvent and chemical productions can be tuned by varying the reaction temperatures and tuning the catalyst, all of which provides a flexible process to produce the desired products to meet the market demand. The methods described herein also have the potential to significantly lower the cost of jet fuel production.

DETAILED DESCRIPTION OF THE INVENTION

Figure 1:
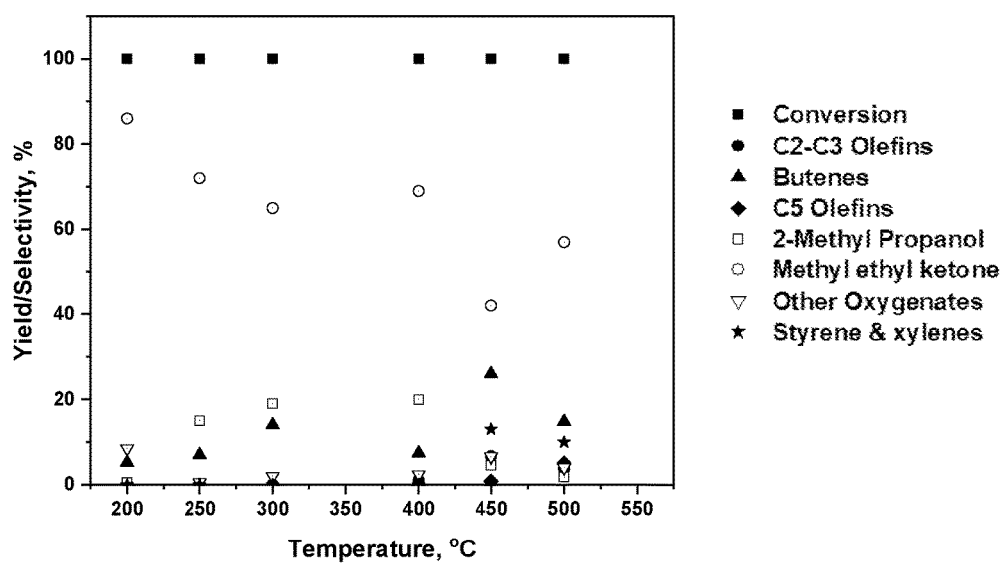
FIG. 1. Graph showing the yield (selectivity) of various products (e.g., $C_2$-$C_3$ olefins, butenes, $C_5$ olefins, 2-methyl propanal, methyl ethyl ketone, styrene and xylenes) vs. temperature for conversion of 2,3-BDO using $SiO_2@ZrO_2$ core-shell catalyst. Reaction conditions: ambient pressure, WHSV=1.0 $h^{-1}$.

The present disclosure is directed to a method for producing one or more hydrocarbon compounds from at least one of 2,3-butanediol, acetoin, and ethanol (collectively referred to as "organic species") by contacting one or more of the foregoing organic species with a catalyst, as further described below, at a temperature of at least 100° C. and up to 500° C. The catalyst may make contact with one or more of the foregoing organic species, with the organic species being in solution (typically, aqueous) or in the gas phase. In some embodiments, the catalyst makes contact with only one or two of 2,3-butanediol, acetoin, or ethanol, wherein any of the foregoing organic species may be in substantially pure form or admixed with a solvent, such as water. In other embodiments, the catalyst makes contact with all three of the foregoing organic species, which are in admixture, such as found in a butanediol fermentation mixture, which is aqueous-based. In the case of an aqueous solution containing 2,3-butanediol, acetoin, and/or ethanol, the aqueous solution may contain water in an amount of, for example, at least or above 5, 10, 20, 30, 40, 50, 60, 70, 75, or 80 wt % (or vol %). Biomass conversion to 2,3-butanediol is well known in the art, e.g., S. K. Garg et al., *Bioresource Technology*, 51(2-3), 103-109, 1995; X.-J. Ji et al., *Biotechnology Advances*, 29(3), 351-364, May-June 2011; and S. Cho et al., *PLoS ONE* 10(9): e0138109. https://doi.org/10.1371/journal.pone.0138109 (2015). The butanediol fermentation mixture results from fermentation of biomass or a sugar (e.g., glucose) to produce 2,3-butanediol, acetoin, ethanol, and a number of other compounds in smaller amounts. In some embodiments, the catalyst may be contacted with a crude or partially purified butanediol fermentation mixture.

As indicated above, the method produces one or more hydrocarbon compounds from at least one of 2,3-butanediol, acetoin, and ethanol. The term "hydrocarbon compounds," as used herein, refers to compounds containing carbon and hydrogen, and optionally, one or more heteroatoms (typically oxygen), and wherein the hydrocarbon compound is different than the starting organic species (2,3-butanediol, acetoin, and ethanol). Some examples of hydrocarbon compounds that can be produced by the methods described herein include $C_2$-$C_8$ mixed olefins, or alkenes containing 2-8 carbon atoms (particularly $C_4$ unsaturated compounds, and more particularly, the butenes), methyl ethyl ketone (MEK), 1,3-butadiene, 2-methyl propanal, acetone, styrene, and xylenes. Some examples of $C_4^+$ alkenes include 1-butene, 2-butene, 1-pentene, cis-2-pentene, trans-2-pentene, isopentene (3-methyl-1-butene), 1-hexene, cis-2-hexene, trans-2-hexene, cis-3-hexene, trans-3-hexene, isohexene (4-methyl-1-pentene), 3-methyl-1-pentene, 3,4-dimethyl-1-pentene, 1-heptene, isoheptene (5-methyl-1-hexene), 4-methyl-1-hexene, and 1-octene, 2,4,4-trimethyl-1-pentene. The methods described herein may produce one or more of any of the foregoing compounds. In some embodiments, by appropriate choice of the catalyst and process conditions (e.g., temperature), the method produces predominantly one type of product, wherein the term "predominantly" generally corresponds to a yield of greater than 50%, although, in some cases, a yield of at least 40%, 45%, or 50% may correspond to a predominant amount. For example, in some embodiments, $C_2$-$C_8$ mixed olefins (particularly $C_4$ unsaturated compounds, and more particularly, the butenes) are produced in at least or greater than 40%, 45%, or 50% yield; or MEK is produced in at least or greater than 40%, 45%, or 50% yield; or 1,3-butadiene is produced in at least or greater than 40%, 45%, or 50% yield. In some embodiments, the yield for any of the foregoing compounds may be at least or greater than, for example, 55%, 60%, 65%, 70%, 75%, 80%, 85%, or 90%.

In the process, a suitable reaction temperature is employed during contact of the of the one or more organic species with the catalyst. Generally, the reaction temperature is at least 100° C. and up to 500° C. In different embodiments, the reaction temperature is precisely or about, for example, 100° C., 125° C., 150° C., 175° C., 200° C., 225° C., 250° C., 275° C., 300° C., 325° C., 350° C., 375° C., 400° C., 425° C., 450° C., 475° C., or 500° C., or a temperature within a range bounded by any two of the foregoing exemplary temperatures, e.g., 100° C.-500° C., 200° C.-500° C., 300° C.-500° C., 350° C.-500° C., 400° C.-500° C., 100° C.-400° C., 200° C.-400° C., 300° C.-400° C., 100° C.-300° C., 200° C.-500° C., 250° C.-500° C., 300° C.-500° C., 200° C.-450° C., 250° C.-450° C., or 300° C.-450° C.). Generally, ambient (i.e., normal atmospheric) pressure of about 1 atm is used in the method described herein. However, in some embodiments, an elevated pressure or reduced pressure may be used. For example, in some embodiments, the pressure may be elevated to, for example, 1.5, 2, 3, 4, or 5 atm, or reduced to, for example, 0.5, 0.2, or 0.1 atm.

In a first set of embodiments, the catalyst is composed of nanoparticles containing (a) a first metal oxide selected from at least one (i.e., one or more) of zirconium oxide, cerium oxide, titanium oxide, and lanthanum oxide, and (b) at least one main group metal oxide. The foregoing catalyst is herein also referred to as the "first catalyst". The nanoparticles typically have a size of up to or less than 1000 nm, and more typically, at least 1, 2, or 5 nm and up to 10, 15, 20, 30, 40, 50, 100, 200, or 500 nm. The main group metal oxide refers to oxides of elements corresponding to Groups 13-15 of the Periodic Table. Some examples of main group metal oxides include silicon dioxide, aluminum oxide, gallium oxide, indium oxide, germanium oxide, tin oxide, lead oxide, arsenic oxide, antimony oxide, and bismuth oxide. In some embodiments, the main group metal oxide is composed of solely or at least silicon dioxide and/or aluminum oxide. In different embodiments, the nanoparticles of the catalyst contain at least zirconium oxide in combination with one or more of the main group metal oxides provided above, or at least cerium oxide in combination with one or more of the main group metal oxides provided above, or at least titanium oxide in combination with one or more of the main group metal oxides provided above, or at least lanthanum oxide in combination with one or more of the main group metal oxides provided above. In further embodiments, any of the nanoparticle compositions described above may or may not also include copper ions or silver ions, either within the nanoparticles or on surfaces of the nanoparticles, provided that component (a) is not completely covered by the copper or silver ions (or other species). Nanoparticle compositions where copper or silver ions are included have herein been found to have an enhanced ability to more selectively produce butenes.

In some embodiments, the nanoparticles of the first catalyst described above further include: (c) an auxiliary metal oxide selected from at least one of zinc oxide, alkali oxides, and alkaline earth oxides. Some examples of alkali oxides include lithium oxide, sodium oxide, potassium oxide, and rubidium oxide. Some examples of alkaline earth oxides include magnesium oxide, calcium oxide, strontium oxide, and barium oxide. In different embodiments, the nanoparticles of the first catalyst contain at least zirconium oxide in combination with one or more of the main group metal oxides provided above in further combination with one or more of the auxiliary metal oxides provided above, or at least cerium oxide in combination with one or more of the main group metal oxides provided above in further combination with one or more of the auxiliary metal oxides provided above, or at least titanium oxide in combination with one or more of the main group metal oxides provided above in further combination with one or more of the auxiliary metal oxides provided above, or at least lanthanum oxide in combination with one or more of the main group metal oxides provided above in further combination with one or more of the auxiliary metal oxides provided above. In further embodiments, any of the nanoparticle compositions described above may or may not also include copper ions or silver ions, as discussed above.

In some embodiments, at least components (a) and (b) in nanoparticles of the first catalyst are homogeneously integrated with each other within the nanoparticles. In other embodiments, the nanoparticles have a core-shell structure containing a core composed of component (b), which is at least one of the main group metal oxides, and a shell composed of component (a), which is at least one of the first metal oxides (i.e., at least one of zirconium oxide, cerium oxide, titanium oxide, or lanthanum oxide), wherein it is understood that the shell at least partially encapsulates the core. In different embodiments, the nanoparticles of the catalyst contain at least zirconium oxide in the shell in combination with one or more of the main group metal oxides provided above in the core, or at least cerium oxide in the shell in combination with one or more of the main group metal oxides provided above in the core, or at least titanium oxide in the shell in combination with one or more of the main group metal oxides provided above in the core, or at least lanthanum oxide in the shell in combination with one or more of the main group metal oxides provided above in the core. The core-shell nanoparticles may also include one or more auxiliary metal oxides corresponding to component (c), either in the core or shell, or in both. Component (c) may be homogeneously integrated into the core containing component (b) or into the shell containing component (a), or component (c) may be included as an intermediate layer between the core and shell. However, component (c) or other material should not completely encapsulate component (a), since, for purposes of the invention, component (a) should be able to make contact with the organic species being converted to hydrocarbons. In further embodiments, any of the nanoparticle compositions described above may or may not also include copper ions or silver ions, either throughout the bodies of the nanoparticles or on surfaces of the nanoparticles.

Compositions pertaining to the first catalyst, as described above, can be synthesized by methods well known in the art. Metal oxide nanoparticles can be produced by a number of sol-gel and hydrothermal methods well known in the art, e.g., H. S. Lim, et al., *AIP Conference Proceedings*, 1571, 812 (2013) and S. Sagadevan et al., *Journal of Materials Science: Materials in Electronics*, 27(6), 5622-5627, June 2016, the contents of which are herein incorporated by reference. Methods for producing core-shell versions of such metal oxide nanoparticles, such as by co-precipitation and seeded polymerization, are also well known in the art, e.g., N. Selvi et al., *Journal of Materials Science: Materials in Electronics*, 25(11), 5078-5083, November 2014; V. V. Srdic et al., *Processing and Application of Ceramics*, 7(2), 45-62, 2013; and P. M. Arnal et al., *Chem. Mater.*, 18(11), 2733-2739, 2006, the contents of which are herein incorporated by reference.

In some embodiments, the first catalyst described above is used in combination with scandium oxide ($Sc_2O_3$) to more selectively produce 1,3-butadiene from the one or more organic species (particularly 2,3-butanediol). In a first embodiment, the scandium oxide is in admixture with the first catalyst (e.g., the core-shell version of the first catalyst) during the conversion process of 2,3-butanediol. In a second embodiment, a two-stage process is employed in which the 2,3-butanediol is first reacted with scandium oxide to produce intermediate products that are then reacted with the first catalyst (e.g., the core-shell version of the first catalyst). In other embodiments, the first catalyst is used without scandium oxide, and generally without copper or silver, to more selectively produce methyl ethyl ketone (MEK). The present invention is also directed to methods for regenerating the first catalyst, such as by calcining the first catalyst under air and about 550° C. for at least 2 hours.

In a second set of embodiments, the catalyst is composed of a zeolite loaded with at least one metal selected from copper, silver, nickel, palladium, platinum, rhodium, and ruthenium in an amount of 1-30 wt % by weight of the zeolite. The foregoing catalyst is herein also referred to as the "second catalyst". The total amount of any one or more of the foregoing active metals that are present in the catalyst may be, for example, 1, 2, 5, 10, 15, 20, 25, or 30 wt %, or in an amount within a range bounded by any two of the foregoing amounts. The zeolite considered herein can be any of the porous aluminosilicate structures known in the art that are stable under high temperature conditions, i.e., of at least 100° C., 150° C., 200° C., 250° C., 300° C., and higher temperatures up to, for example, 500° C., 550° C., 600° C., 650° C., 700° C., 750° C., 800° C., 850° C., or 900° C. In particular embodiments, the zeolite is stable from at least 100° C. and up to 700° C. Typically, the zeolite is ordered by having a crystalline or partly crystalline structure. The zeolite can generally be described as a three-dimensional framework containing silicate ($SiO_2$ or $SiO_4$) and aluminate ($Al_2O_3$ or $AlO_4$) units that are interconnected (i.e., cross-linked) by the sharing of oxygen atoms. The zeolite can be microporous (i.e., pore size of less than 2 μm), mesoporous (i.e., pore size within 2-50 μm, or sub-range therein), or a combination thereof.

In various embodiments, the zeolite is a MFI-type zeolite, MWW-type zeolite, MEL-type zeolite, MTW-type zeolite, MCM-type zeolite, BEA-type zeolite, kaolin, or a faujasite-type of zeolite. Some particular examples of zeolites include the pentasil zeolites, and more particularly, the ZSM class of zeolites (e.g., ZSM-5, ZSM-8, ZSM-11, ZSM-12, ZSM-15, ZSM-23, ZSM-35, ZSM-38, ZSM-48), zeolite X, zeolite Y, zeolite beta, and the MCM class of zeolites (e.g., MCM-22 and MCM-49). The compositions, structures, and properties of these zeolites are well-known in the art, and have been described in detail, as found in, for example, U.S. Pat. Nos. 4,721,609, 4,596,704, 3,702,886, 7,459,413, and 4,427,789, the contents of which are incorporated herein by reference in their entirety. The zeolite can also have any suitable silicato-alumina (i.e., $SiO_2/Al_2O_3$ or "Si/Al") ratio. For example, the zeolite can have a Si/Al ratio of precisely, at least, more than, less than, or up to 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 120, 150, or 200, or a Si/Al ratio within a range bounded by any two of the foregoing values. In some embodiments, the zeolite is a 2D pillared zeolite, as well known in the art. The 2D pillared zeolite can be a 2D pillared version of any of the zeolites described above, such as a pillared MFI or MWW zeolite.

Typically, the zeolite contains an amount of cationic species, aside from the active species mentioned above, for the second catalyst. As is well known in the art, the amount of cationic species is generally proportional to the amount of aluminum in the zeolite. This is because the replacement of silicon atoms with lower valent aluminum atoms necessitates the presence of countercations to establish a charge balance. Some examples of cationic species include hydrogen ions ($H^+$), alkali metal ions, alkaline earth metal ions, and main group metal ions. Some examples of alkali metal ions that may be included in the zeolite include lithium ($Li^+$), sodium ($Na^+$), potassium ($K^+$), rubidium ($Rb^+$), and cesium ($Cs^+$). Some examples of alkaline earth metal ions that may be included in the zeolite include ($Be^{2+}$), magnesium ($Mg^{2+}$), calcium ($Ca^{2+}$), strontium ($Sr^{2+}$), and barium ($Ba^{2+}$). Some examples of main group metal ions that may be included in the zeolite include boron ($B^{3+}$), gallium ($Ga^{3+}$), indium ($In^{3+}$), and arsenic ($As^{3+}$). In some embodiments, a combination of cationic species is included. The cationic species can be in a trace amount (e.g., no more than 0.01 or 0.001%), or alternatively, in a significant amount (e.g., above 0.01%, and up to, for example, 0.1, 0.5, 1, 2, 3, 4, or 5% by weight of the zeolite). In some embodiments, any one or more of the above classes or specific examples of cationic species are excluded from the zeolite.

Generally, the zeolite catalyst described herein is in the form of a powder. In a first set of embodiments, at least a portion, or all, of the particles of the powder have a size less than a micron (i.e., nanosized particles). The nanosized particles can have a particle size of precisely, at least, up to, or less than, for example, 1, 2, 5, 10, 20, 30, 40, 50, 60, 70, 80, 90, 100, 150, 200, 250, 300, 350, 400, 450, 500, 550, 600, 650, 700, 750, 800, 850, 900, or 950 nanometers (nm), or a particle size within a range bounded by any two of the foregoing values. In a second set of embodiments, at least a portion, or all, of the particles of the powder have a size at or above 1 micron in size. The micron-sized particles can have a particle size of precisely, at least, up to, or less than, for example, 1, 2, 5, 10, 20, 30, 40, 50, 60, 70, 80, 90, or 100 microns (μm), or a particle size within a range bounded by any two of the foregoing values. In some embodiments, single crystals or grains of the catalyst correspond to any of the sizes provided above, while in other embodiments, crystals or grains of the catalyst are agglomerated to provide agglomerated crystallites or grains having any of the above exemplary dimensions.

In other embodiments, the zeolite catalyst can be in the form of a film, a coating, or a multiplicity of films or coatings. The thickness of the coatings or multiplicity of coatings can be, for example, 1, 2, 5, 10, 50, or 100 microns, or a range therein, or up to 100 micron thickness. In yet other embodiments, the zeolite catalyst is in the form of a non-particulate (i.e., continuous) bulk solid. In still other embodiments, the zeolite catalyst can be fibrous or in the form of a mesh.

Compositions pertaining to the second catalyst, as described above, can be synthesized by methods well known in the art. The method may incorporate the metal ions homogeneously into the zeolite or as a coating on surfaces of the zeolite. The zeolite may be a single type of zeolite, or a combination of different zeolite materials. In particular embodiments, the catalyst described herein is prepared by, first, impregnating the zeolite with the one or more metals to be loaded. The impregnating step can be achieved by, for example, treating the zeolite with one or more solutions containing salts of the metals to be loaded. The metal-containing solution is contacted with the zeolite such that the solution is absorbed into the zeolite, preferably into the entire volume of the zeolite. Typically, in preparing the metal-loaded zeolite catalyst, the acid zeolite form (i.e., H-ZSM5) or its ammonium salt (e.g., $NH_4$-ZSM-5) is used as a starting material on which an exchange with metal ions (e.g., copper ions) is performed. The particulars of such metal exchange processes are well known in the art. In one embodiment, the impregnating step is achieved by treating the zeolite with a solution that contains all of the metals to be loaded. In another embodiment, the impregnating step is achieved by treating the zeolite with two or more solutions, wherein the different solutions contain different metals or combinations of metals. Each treatment of the zeolite with an impregnating solution corresponds to a separate impregnating step. Typically, when more than one impregnating step is employed, a drying and/or thermal treatment step is employed between the impregnating steps. The preparation of a number of types of zeolites, including pillared forms of two-dimensional zeolites, is described in, for example, W. J. Roth et al., *Chem. Rev.*, 114, 4807-4837, 2014, the contents of which are herein incorporated by reference. Other methods can be used, such as an ammonia evaporation method, as further described in the Examples section.

Any of the catalysts described above can also be mixed with or affixed onto a support material suitable for the conditions of the conversion reaction. The support material can be a powder (e.g., having any of the above particle sizes), granular (e.g., 0.5 mm or greater particle size), a bulk material, such as a honeycomb monolith of the flow-through type, a plate or multi-plate structure, or corrugated metal sheets. If a honeycomb structure is used, the honeycomb structure can contain any suitable density of cells. For example, the honeycomb structure can have 100, 200, 300, 400, 500, 600, 700, 800, or 900 cells per square inch (cells/in$^2$) (or from 62-140 cells/cm$^2$) or greater. The support material is generally constructed of a refractory composition, such as those containing cordierite, mullite, alumina (e.g., α-, β-, or γ-alumina), or zirconia, or a combination thereof. Honeycomb structures, in particular, are described in detail in, for example, U.S. Pat. Nos. 5,314,665, 7,442, 425, and 7,438,868, the contents of which are incorporated herein by reference in their entirety. When corrugated or other types of metal sheets are used, these can be layered on top of each other with catalyst material supported on the sheets such that passages remain that permit the flow of the liquid or gas containing the organic species undergoing conversion. The layered sheets can also be formed into a structure, such as a cylinder, by winding the sheets.

The catalyst and reactor can have any of the designs known in the art for catalytically treating a fluid or gas at elevated temperatures, such as a fluidized bed reactor. The process may be in a continuous or batch mode. In particular embodiments, the one or more organic species are injected into a heated reactor such that the one or more organic species are quickly volatilized into gas, and the gas passed over the catalyst. In some embodiments, the reactor design includes a boiler unit and a reactor unit if the fermentation stream is used directly as a feedstock without purification. The boiler unit is generally not needed if the fermentation stream is distilled to concentrate one or more organic species because the distillation process removes the dissolved solids in the fermentation streams. The boiler unit volatilizes liquid feedstock into gases prior to entry into the reactor unit and withholds dissolved solids.

In some embodiments, the conversion method described above is integrated with a biomass-to-butanediol fermentation process, wherein the fermentation process produces the one or more organic species used as feedstock for the conversion process. By being "integrated" is meant that one or more organic species produced at a fermentation facility or zone is sent to and processed at a conversion facility or zone that performs the conversion process described above. Preferably, in order to minimize production costs, the fermentation process is in close enough proximity to the conversion facility or zone, or includes appropriate conduits for transferring produced organic compounds to the conversion facility or zone, thereby not requiring the organic compounds to be shipped. In particular embodiments, the fermentation stream produced in the fermentation facility is directly transferred to the conversion facility, generally with removal of solids from the raw stream (generally by filtration or settling) before contact of the stream with the first or second catalyst.

In some embodiments, the fermentation process is performed in an autonomous fermentation facility, i.e., where saccharides, produced elsewhere, are loaded into the fermentation facility to produce the one or more organic species. In other embodiments, the fermentation process is part of a larger biomass reactor facility, i.e., where biomass is decomposed into fermentable saccharides, which are then processed in a fermentation zone. Biomass reactors and fermentation facilities are well known in the art. Biomass generally refers to lignocellulosic matter (i.e., plant material), such as wood, grass, leaves, paper, corn husks, sugar cane, bagasse, and nut hulls. Generally, biomass-to-butanediol conversion is performed by 1) pretreating biomass under well-known conditions to loosen lignin and hemicellulosic material from cellulosic material, 2) breaking down cellulosic material into fermentable saccharide material by the action of a cellulase enzyme, and 3) fermentation of the saccharide material, by the action of an organism capable of fermenting saccharide to 2,3-butanediol. In other embodiments, the one or more organic species are produced from a more direct sugar source, such as a plant-based source of sugars, such as sugar cane or a grain starch (such as corn starch).

The present disclosure is also directed to methods for further converting any of the hydrocarbon compounds (e.g., butenes, 1,3-butadiene, and MEK) produced by the conversion process described above to a synthetic fossil fuel (e.g., jet fuel), fuel additive, or commodity chemical. To effect the further conversion, the hydrocarbon compounds are reacted with one or more additional catalysts known in the art capable of such transformation. The additional catalyst may be, for example, a zeolite (e.g., H-BEA, H-ZSM-5, MCM, H-ZSM-22, or H-ZSM-57), amorphous aluminosilicate, sulfonic acid ion-exchange resin (e.g., Amberlyst® 15, Amberlyst® 35, Amberlyst® 36, Purolite®, Dowex®, Lewatit®), or solid phosphoric acid. The conditions of the reaction may be, for example, 100-500° C. (or more particularly, 70-350° C.), 1-60 atm, a weight hourly space velocity (WHSV) of 0.1 $h^{-1}$ to 20 $h^{-1}$, and an inert or hydrogen carrier gas. The foregoing catalysts and conditions are generally suited for a dimerization, oligomerization, or dehydrocyclization process. However, the process may also include a hydrogenation process, which may employ an oxide catalyst (e.g., $Al_2O_3$, $TiO_2$, $CeO_2$, or $ZrO_2$) coated or impregnated with platinum (Pt), nickel (Ni), rhodium (Rh), ruthenium (Ru) or other noble metal or precious metal. In some embodiments, zinc (Zn) or phosphorus (P) is included in the zeolite (e.g., ZSM-5) to make the catalyst more selective for converting butenes to one or more of benzene, toluene, and xylenes (particularly p-xylene). In some embodiments, the oligomerization and hydrogenation occur simultaneously, while in other embodiments, the oligomerization and hydrogenation occur in separate steps.

The term "synthetic fossil fuel" refers to a mixture of hydrocarbon compounds useful as a fuel or as a blendstock in a fuel. The mixture of hydrocarbon compounds produced herein substantially corresponds (e.g., in composition and/or properties) to a known petrochemical fuel, such as petroleum, or a fractional distillate of petroleum. Some examples of petrochemical fuels include jet fuel (i.e., jet propellant, such as JP-8), gasoline, kerosene, and diesel. Like hydrocarbon fuel grades in current use, the mixture of hydrocarbon compounds produced herein can, in some embodiments, be predominantly or exclusively composed of alkanes, alkenes, aromatics, or a mixture thereof. Although aromatics (particularly benzene) may be present in the hydrocarbon mixture, their presence may be minimized to adhere to current fuel standards. The raw hydrocarbon product may also be fractionated by distillation into different fuel grades, each of which is known to be within a certain boiling point range. A particular advantage of the instant method is its ability to produce such fuel grades in the substantial absence of contaminants (e.g., mercaptans) normally required to be removed during the petroleum refining process. Moreover, by appropriate adjustment of the catalyst and processing conditions, a select distribution of hydrocarbons can be obtained.

Depending on the final composition of the hydrocarbon product, the product can be directed to a variety of applications, including, for example, as precursors for plastics, polymers, and fine chemicals. The process described herein can advantageously produce a range of hydrocarbon products that differ in any of a variety of characteristics, such as molecular weight (i.e., hydrocarbon weight distribution), degree of saturation or unsaturation (e.g., alkane to alkene ratio), and level of branched or cyclic isomers. The process provides this level of versatility by appropriate selection of, for example, composition of the catalyst (e.g., catalytic metal), amount of catalyst (e.g., ratio of catalyst to alcohol precursor), processing temperature, and flow rate (e.g., LHSV).

Examples have been set forth below for the purpose of illustration and to describe certain specific embodiments of the invention. However, the scope of this invention is not to be in any way limited by the examples set forth herein.

Example 1

Preparation and Characterization of a Core-Shell $SiO_2$@$ZrO_2$ Catalyst for 2,3-BDO Upgrading Catalyst Synthesis Core-shell $SiO_2$@$ZrO_2$ particles were synthesized in a four-step procedure. First, silica spheres were prepared using the known Stöber process. The silica particles were then dispersed in ethanol and Lutensol® AO5 (a non-ionic ethoxylated surfactant), and zirconium butoxide was added. The reaction proceeded overnight at 303K. Exchange with water was performed by centrifuge and re-dispersing in water. Third, the particles were aged in water at 293K for 3 days. Next, calcination at 1173K was performed to remove the organic materials.

Catalysis Reaction Conditions

For the catalysis tests, approximately 150 mg of catalyst was loaded in a fixed bed reactor. Then the catalyst was heated to reaction temperature under helium flow. BDO or a mixture of BDO, acetoin, and ethanol was fed into the reactor using a syringe pump, and the products obtained were analyzed using gas chromatography-flame ionization detection (GC-FID).

Results and Discussion

Core-shell $SiO_2@ZrO_2$ catalyst was used to convert aqueous 2,3-BDO (95 wt % water). The yield (selectivity) of various products (e.g., $C_2$-$C_3$ olefins, butenes, $C_5$ olefins, 2-methyl propanal, methyl ethyl ketone, styrene and xylenes) were determined and the data plotted vs. temperature in the graph shown in FIG. 1. Reaction conditions included ambient pressure and a weight hourly space velocity (WHSV) of 1.0 $h^{-1}$. As shown in FIG. 1, the major product is methyl ethyl ketone with other minor products, such as butenes, 2-methyl propanal, $C_2$-$C_3$ olefins, etc. Maximum yield of methyl ethyl ketone was achieved at 200° C.

Figure 2:
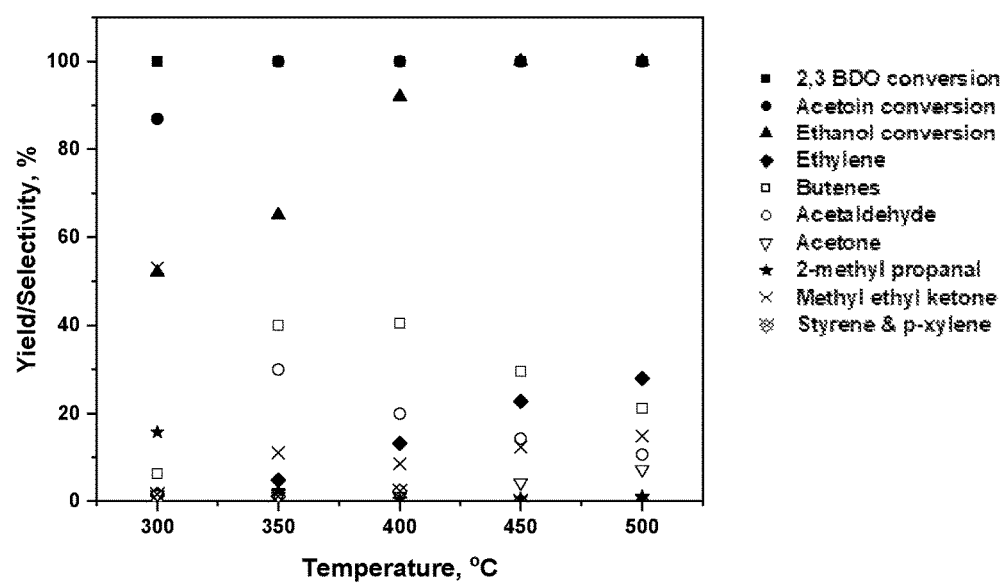
FIG. 2. Graph showing the product distribution from converting a mixture of 2,3-BDO, acetoin, and ethanol using a core-shell $SiO_2@ZrO_2$ catalyst as a function of temperature. Reaction conditions: ambient pressure, WHSV=1.0 $h^{-1}$.

An aqueous mixture of 2,3-BDO (10%), acetoin (10%) and ethanol (20%) in water (60%) was also tested over core-shell $SiO_2@ZrO_2$ catalyst. Reaction conditions included ambient pressure and a WHSV of 1.0 $h^{-1}$. FIG. 2 shows the product distribution from converting a mixture of 2,3-BDO, acetoin and ethanol using core-shell $SiO_2@ZrO_2$ catalyst. As shown in FIG. 2, above 250° C., 2,3-BDO conversion was 100%, while a temperature of 350° C. and 450° C. was needed to completely convert acetoin and ethanol, respectively. The major products include methyl ethyl ketone, butenes, acetaldehyde and ethylene.

Example 2

Preparation and Characterization of a Copper-Zeolite Catalyst for 2,3-BDO Upgrading Catalyst Synthesis Copper was loaded onto zeolites by using an ammonia evaporation method. In a typical method for 20% Cu loading over 1 g of zeolite, a required amount of copper nitrate was dissolved in 4 mL of water and the pH of the solution was maintained at 9.1 by adding ammonia solution. Then, the final volume was adjusted to 8 mL by adding deionized water. After that, 1 g of zeolite sample was added to it and magnetically stirred at room temperature for 4 hours for an even distribution of Cu over zeolite. Finally, the solution was kept at 80° C. for 1.5 hours before collecting the solid mass by centrifugation. During the centrifugation step, the solid was washed with copious amounts of deionized water until the pH of the solution reached 7. Then the solid mass was dried in an oven overnight at 80° C. Finally, the catalyst was obtained after calcining the dried mass at 550° C. for four hours. Different amounts of Cu loading were varied by using a corresponding amount of copper nitrate.

Catalysis Reaction Conditions

For the catalysis tests, approximately 150 mg of catalyst was loaded in a fixed bed reactor. Then the catalyst was heated to 300° C. under hydrogen flow to reduce all the oxides of copper into metallic copper. After that, the temperature was lowered to reaction temperature (250° C.). BDO was fed into the reactor heated at 250° C. and the products obtained were monitored by using GC-FID.

Results and Discussion

Figure 3A:
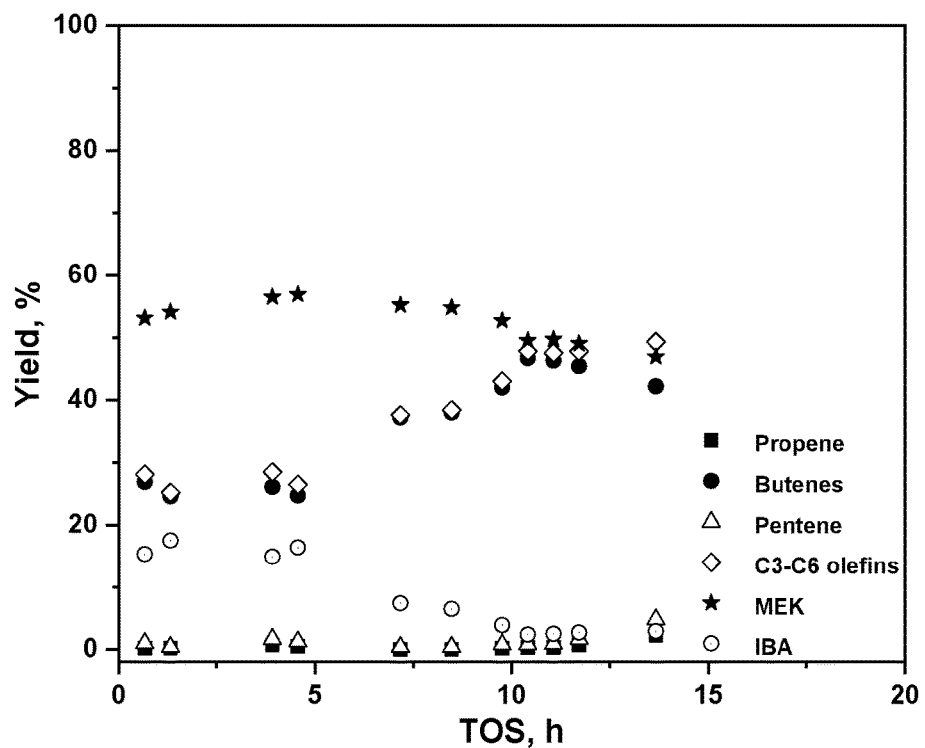
FIGS. 3A-3C. Graphs showing the product distribution of BDO conversion using Cu/BEA, Cu/ZSM-5 and Cu/P-MFI zeolite catalysts, respectively. Reaction conditions: 250° C., ambient pressure, WHSV=1.0 $h^{-1}$.
Figure 3B:
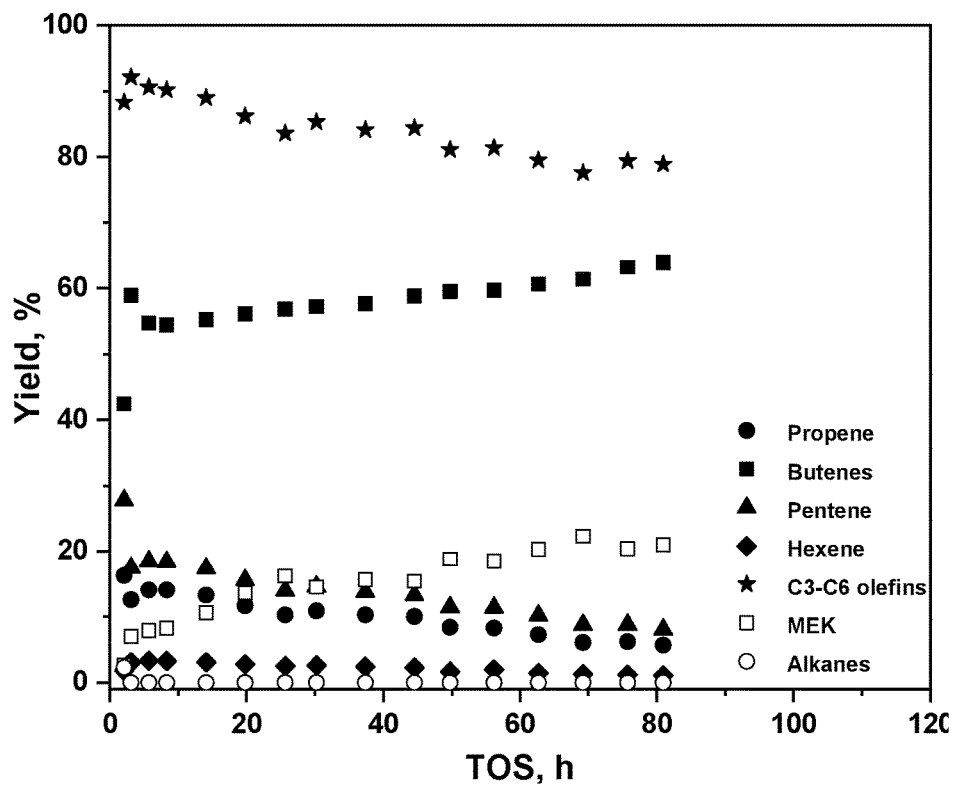
Figure 3C:
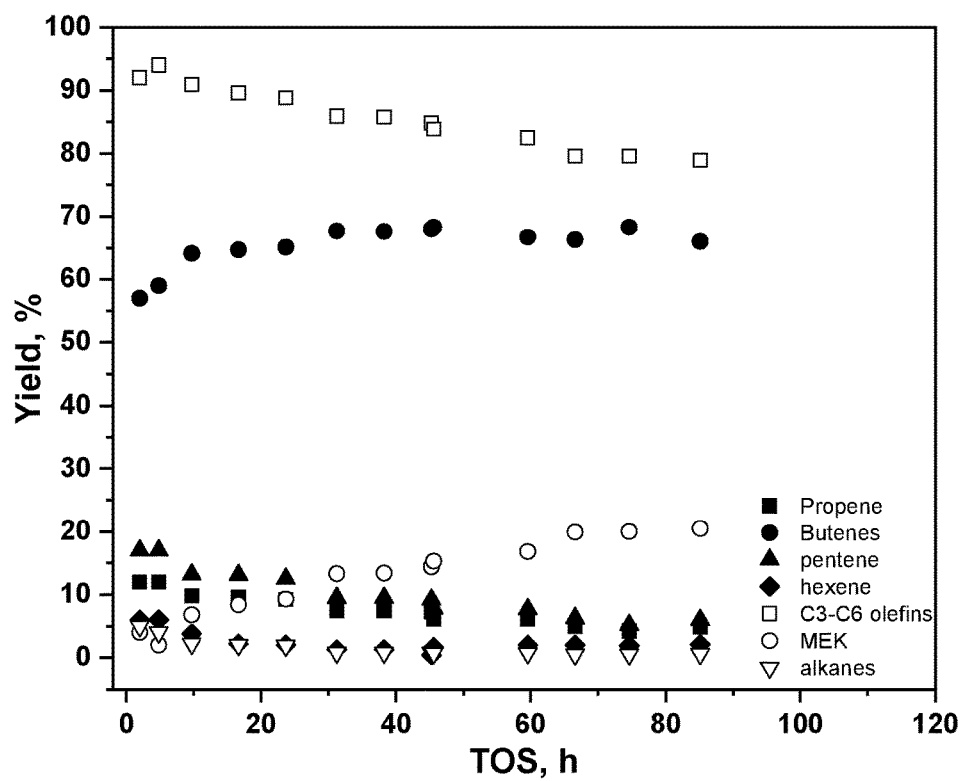

The catalytic conversion of commercial BDO was tested with different catalysts. Reaction conditions included 250° C., ambient pressure, and WHSV of 1.0 $h^{-1}$. FIGS. 3A, 3B, and 3C show the product distribution of BDO conversion using Cu/BEA, Cu/ZSM-5 and Cu/P-MFI zeolite catalysts, respectively. In the case of Cu/BEA, the production of MEK is high in the range of 50%, even after 10 hours of reaction, while the production of it is minimum in Cu/ZSM-5 and Cu/PMFI samples. Similarly, the butene production reaches above 65% in both of these later samples.

Figure 4A:
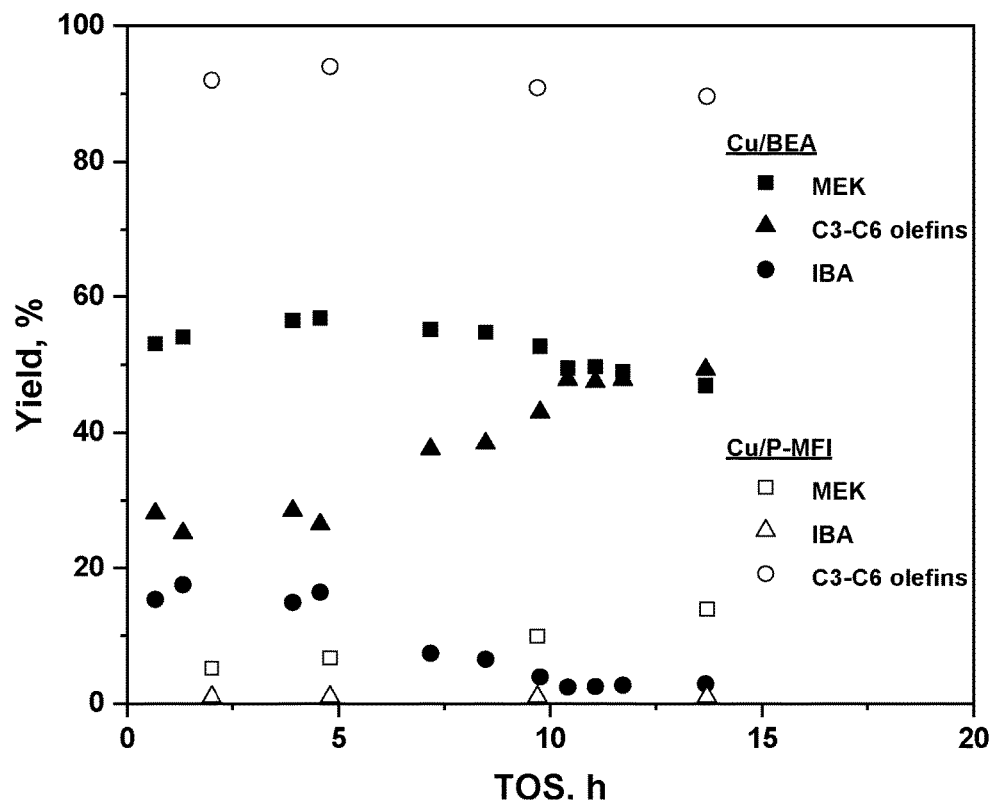
FIGS. 4A-4B. Graphs showing comparative product distribution for Cu/P-MFI, Cu/BEA and Cu/ZSM-5 for BDO conversion. Reaction conditions: ambient pressure, WHSV=1.0 $h^{-1}$.
Figure 4B:
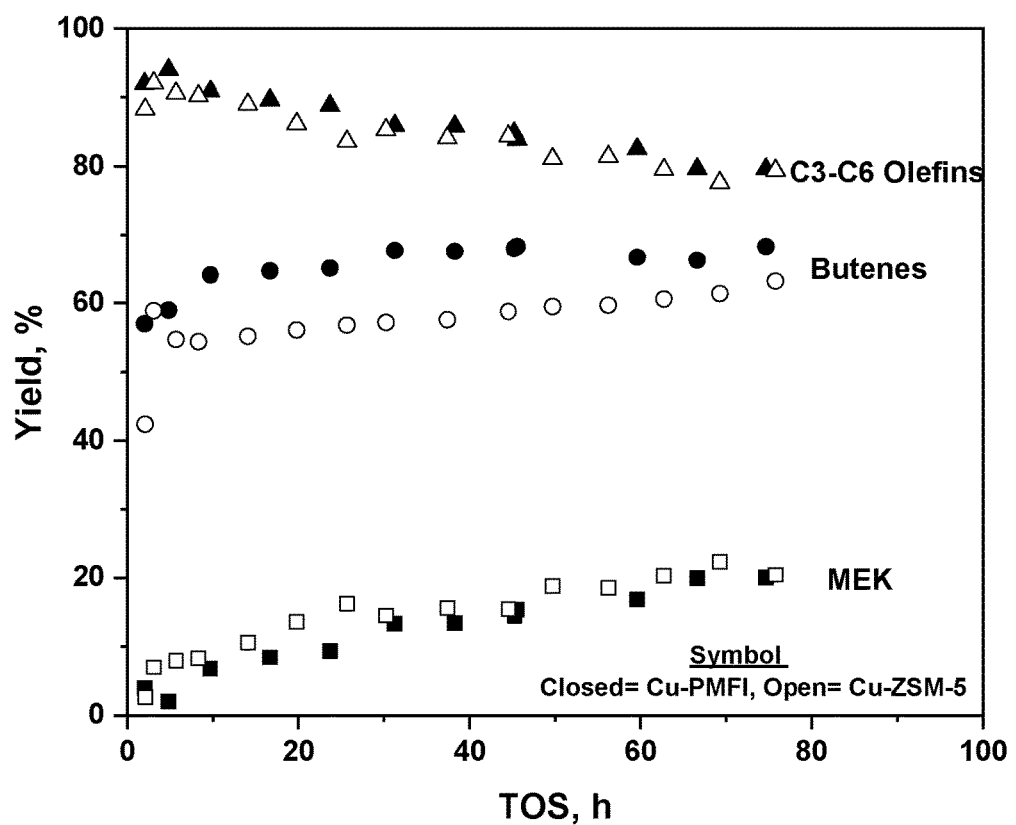

FIGS. 4A and 4B show comparative product distribution for Cu/P-MFI, Cu/BEA and Cu/ZSM-5 for BDO conversion. Reaction conditions included 250° C., ambient pressure, and WHSV of 1.0 $h^{-1}$. Based on the first 14 hours reaction data shown in FIG. 4A, it is evident that $C_3$-$C_6$ olefins production using Cu/P-MFI catalyst is almost double that of Cu/BEA catalyst. Methyl ethyl ketone (MEK) production is also significantly higher for the Cu/BEA catalyst, which suggests that hydrogenation activity of Cu on BEA is lower than that on P-MFI. On the other hand, the total amounts of $C_3$-$C_6$ olefins produced by using Cu/ZSM-5 are similar to the total amounts of $C_3$-$C_6$ olefins produced by Cu/P-MFI catalyst (FIG. 4B). As can also be seen, the production of butene is better in the case of the Cu/P-MFI catalyst, which suggests that Cu/ZSM-5 converts more butenes to other olefins.

The Cu/zeolite catalyst can be used to convert a mixture of 2,3-BDO and acetoin. As shown in Table 1 below, similar product distribution can be obtained from the mixture of 2,3-BDO and acetoin compared with feeding only 2,3-BDO. This means acetoin can be converted to the same products as obtained from 2,3-BDO.

TABLE 1

Product comparison between using 2,3-BDO and mixture of 2,3-BDO and acetoin

|  | 2,3-BDO | 2,3-BDO + acetoin |
|---|---|---|
| Propene | 9.8 | 9.5 |
| Butenes | 64.1 | 65.9 |
| Pentenes | 13.2 | 13.1 |
| Hexenes | 3.8 | 2.2 |
| MEK | 6.8 | 6.5 |
| $C_1$-$C_3$ light paraffins | 2.2 | 2.7 |

Conditions: Cu/P-MFI, 250° C., WHSV = 1.0 h−1; 2,3-BDO:acetoin (1.7:1, weight ratio).

While there have been shown and described what are at present considered the preferred embodiments of the invention, those skilled in the art may make various changes and modifications which remain within the scope of the invention defined by the appended claims.

What is claimed is:

1. A method for producing one or more hydrocarbon compounds from a reactant source comprising 2,3-butanediol or acetoin, the method comprising contacting said reactant source with a catalyst at a temperature of at least 100° C. and up to 500° C. to result in said reactant source being converted to said one or more hydrocarbon compounds, wherein said catalyst is either:
    (i) a catalyst comprising nanoparticles composed of (a) a first metal oxide selected from the group consisting of zirconium oxide, cerium oxide, titanium oxide, and lanthanum oxide, and (b) a main group metal oxide; or (ii) a catalyst comprising a zeolite loaded with at least one metal selected from the group consisting of copper, silver, nickel, palladium, platinum, rhodium, and ruthenium in an amount of 1-30 wt % by weight of the zeolite.

2. The method of claim 1, wherein said reactant source is an aqueous solution, and said catalyst is contacted with said aqueous solution at said temperature.

3. The method of claim 1, wherein said reactant source is an aqueous 2,3-butanediol fermentation mixture comprising 2,3-butanediol, acetoin, and ethanol, and said catalyst is contacted with said aqueous 2,3-butanediol fermentation mixture at said temperature.

4. The method of claim 3, wherein said aqueous 2,3-butanediol fermentation mixture contains water in an amount of at least 20 wt %.

5. The method of claim 3, wherein said aqueous 2,3-butanediol fermentation mixture contains water in an amount of at least 50 wt %.

6. The method of claim 1, wherein said catalyst is (i) a catalyst comprising nanoparticles composed of (a) a first metal oxide selected from the group consisting of zirconium oxide, cerium oxide, titanium oxide, and lanthanum oxide, and (b) a main group metal oxide.

7. The method of claim 1, wherein said catalyst is (i) a catalyst comprising nanoparticles composed of (a) a first metal oxide selected from the group consisting of zirconium oxide, cerium oxide, titanium oxide, and lanthanum oxide, (b) a main group metal oxide, and (c) an auxiliary metal oxide selected from the group consisting of zinc oxide, alkali oxides, and alkaline earth oxides.

8. The method of claim 6, wherein said first metal oxide comprises zirconium oxide.

9. The method of claim 6, wherein said main group metal oxide comprises silicon dioxide, aluminum oxide, or a combination thereof.

10. The method of claim 6, wherein said nanoparticles have a core-shell structure containing a core composed of said main group metal oxide and a shell composed of said first metal oxide selected from the group consisting of zirconium oxide, cerium oxide, titanium oxide, and lanthanum oxide, wherein said shell at least partially encapsulates said core.

11. The method of claim 10, wherein said first metal oxide comprises zirconium oxide.

12. The method of claim 1, wherein said catalyst is (ii) a catalyst comprising a zeolite loaded with at least one metal selected from the group consisting of copper, silver, nickel, palladium, platinum, rhodium, and ruthenium in an amount of 1-30 wt % by weight of the zeolite.

13. The method of claim 12, wherein said zeolite is a pentasil zeolite.

14. The method of claim 13, wherein said pentasil zeolite is a ZSM type of zeolite.

15. The method of claim 12, wherein said zeolite is selected from the group consisting of MFI, BEA, MWW, and zeolite Y types of zeolites.

16. The method of claim 12, wherein said zeolite is a 2D pillared zeolite.

17. The method of claim 16, wherein said 2D pillared zeolite is selected from the group consisting of pillared MFI and MWW zeolites.

18. The method of claim 1, wherein said one or more hydrocarbon compounds includes at least one compound selected from the group consisting of methyl ethyl ketone, alkenes containing 2-8 carbon atoms, 1,3-butadiene, and 2-methylpropanal.

19. The method of claim 1, wherein said one or more hydrocarbon compounds includes butenes and/or 1,3-butadiene produced in greater than 50% yield.

20. The method of claim 1, wherein said one or more hydrocarbon compounds includes methyl ethyl ketone produced in greater than 50% yield.

21. The method of claim 1, further comprising converting the one or more hydrocarbon compounds produced in the process of claim 1 to a synthetic fossil fuel by contacting the one or more hydrocarbon compounds, at a temperature of at least 100° C. and up to 500° C., with an additional catalyst capable of converting the hydrocarbon compounds to a synthetic fossil fuel.

* * * * *